United States Patent [19]

Hazel

[11] Patent Number: 5,025,111
[45] Date of Patent: Jun. 18, 1991

[54] PRODUCTION OF NON-CONJUGATED DIOLEFINS

[75] Inventor: Nicholas J. Hazel, Hull, United Kingdom

[73] Assignee: BP Chemicals Limited, London, England

[21] Appl. No.: 258,477

[22] Filed: Oct. 17, 1988

[30] Foreign Application Priority Data

Oct. 21, 1987 [GB] United Kingdom ................ 8724628

[51] Int. Cl.$^5$ ................................ C07C 2/76
[52] U.S. Cl. ........................ 585/601; 585/646
[58] Field of Search ............................. 585/601, 646

[56] References Cited

U.S. PATENT DOCUMENTS

| | | | |
|---|---|---|---|
| 3,647,902 | 3/1972 | Henrici et al. | 268/690 |
| 3,855,338 | 12/1974 | Fitton et al. | 260/680 |
| 4,454,368 | 6/1984 | Banks | 585/646 |

FOREIGN PATENT DOCUMENTS

| | | |
|---|---|---|
| 0282313 | 9/1988 | European Pat. Off. . |
| 1054864 | 1/1967 | United Kingdom . |
| 1064829 | 4/1967 | United Kingdom . |
| 1089956 | 11/1967 | United Kingdom . |
| 1103976 | 2/1968 | United Kingdom . |
| 1106015 | 3/1968 | United Kingdom . |
| 1111508 | 5/1968 | United Kingdom . |
| 1121806 | 7/1968 | United Kingdom . |
| 1123500 | 8/1968 | United Kingdom . |
| 1159053 | 7/1969 | United Kingdom . |
| 1159056 | 7/1969 | United Kingdom . |
| 1170498 | 11/1969 | United Kingdom . |
| 1228811 | 4/1971 | United Kingdom . |
| 1279254 | 6/1972 | United Kingdom . |
| 1414488 | 11/1975 | United Kingdom . |
| 1482745 | 2/1977 | United Kingdom . |
| 1159055 | 7/1979 | United Kingdom . |
| 2131429A | 6/1984 | United Kingdom . |

OTHER PUBLICATIONS

Condon et al., "Olefinic HydroCarbons" Intro. to Organic Chemistry, Holt, Rinehart & Winston Inc., pp. 84–85.

Fridman, R. A. et al, "Disproportionation of Conjugated Dienes", Bulletin of Academy of Sciences of the USSR Division of Chemical Science, vol. 27, No. 5, part 2, Nov. 1978, p. 1068, Plenum Publishing Corp, SU.

*Primary Examiner*—Curtis R. Davis
*Attorney, Agent, or Firm*—Nixon & Vanderhye

[57] ABSTRACT

Non-conjugated diolefins having the formula:

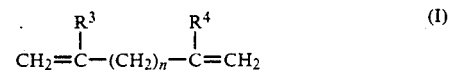

$$CH_2=\underset{\underset{R^3}{|}}{C}-(CH_2)_n-\underset{\underset{R^4}{|}}{C}=CH_2 \quad (I)$$

wherein $R^3$ and $R^4$ are either hydrogen, alkyl or substituted alkyl and n is an integer, are produced by the process comprising reacting a diolefin having the formula:

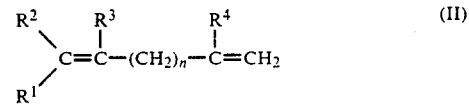

$$\underset{R^1}{\overset{R^2}{\diagdown}}C=\underset{\underset{R^3}{|}}{C}-(CH_2)_n-\underset{\underset{R^4}{|}}{C}=CH_2 \quad (II)$$

wherein $R^3$ and $R^4$ and n are the same as in formula (I) and $R^1$ and $R^2$ are either hydrogen, alkyl or substituted alkyl, with ethylene in the presence of a disproportionation catalyst comprising supported rhenium heptoxide and a promoter comprising either a tetraalkyl tin compound or a trialkyl aluminium compound.

12 Claims, No Drawings

PRODUCTION OF NON-CONJUGATED DIOLEFINS

The present invention relates in general to the production of non-conjugated diolefins and in particular to the production of 2-methyl-1,4-pentadiene (2M-1,4-PD).

Alpha, omega - non-conjugated diolefins are useful in polymer synthesis. Several references to alpha, omega diolefins as reactants in polymerisations refer to 1,5-hexadiene and 1,9-decadiene because both have been available in sample quantities for some time. Their use has been described in the modification of methacrylate polymers, in regulating the molecular weight of stereoregular butadiene rubber, polyalkenmers and polymers of norbornene derivatives, as cross-linking agents in cyclic urethane polymers and in a variety of other applications.

It is known that the reaction of a cyclic olefin with an acyclic olefin in the presence of an olefin disproportionation catalyst can cause ring opening of the cyclic olefin with the formation of an acyclic diene which has a total number of carbon atoms equal to the sum of carbon atoms of the cyclic and acyclic olefins. It is also known that reactions involving ethylene and certain substituted cyclic olefins are frequently unacceptably slow and/or are accompanied by undesirable side reactions which result in a reduced yield of the desired alpha, omega diene. Undesirable side reactions are purportedly reduced by the process of GB-A-1482745 wherein acyclic alpha, omega-dienes of formula:

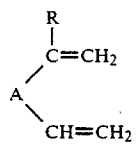

wherein R represents an alkyl group, and A represents a divalent aliphatic group which may optionally bear one or more alkyl substituents and may optionally contain one or more isolated olefinic double bonds are produced by the process comprising reacting a cyclic olefin of formula:

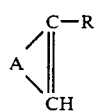

with a beta-olefin of formula:

wherein $R^1$ represents an alkyl group, in the presence of an olefin disproportionation catalyst, to form an intermediate of formula:

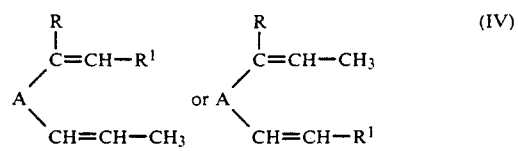

and reacting the intermediate with ethylene. For the reaction of the intermediate of formula (IV) with ethylene it is reported that any disproportionation catalyst may be employed, for example supported rhenium heptoxide.

GB-A-1228811 discloses the disproportionation of ethylene and acyclic mono - and polyenes, for example 1,4-hexadiene, in the presence of promoted metal phosphate catalysts.

We have now found that non-conjugated diolefins and in particular 2M-1,4-PD can be produced from readily available feedstocks. We have also found that although supported rhenium heptoxide catalysts can be used in the process for producing non-conjugated diolefins, their performance in this reaction is considerable improved by the use of tetraalkyl tin or trialkyl aluminium compounds as promoters.

Accordingly, the present invention provides a process for the production of a non-conjugated diolefin having the formula:

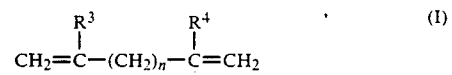

wherein $R_3$ and $R_4$ are either hydrogen, alkyl or substituted alkyl and n is an integer, which process comprises reacting a diolefin having the formula:

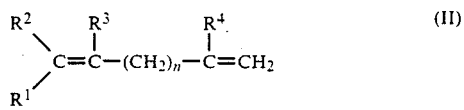

wherein $R^3$ and $R^4$ and n are the same as in formula I and $R^1$ and $R^2$ are either hydrogen, alkyl or substituted alkyl, with ethylene in the presence of a catalyst comprising supported rhenium heptoxide and a promoter comprising either a tetraalkyl tin compound or a trialkyl aluminium compound.

$R^1$, $R^2$, $R^3$ and $R^4$ in the formula (II) are either hydrogen, alkyl or substituted alkyl. Preferred alkyl groups are lower alkyl groups, i.e. $C_1$ to $C_6$ alkyl groups, preferably methyl. The alkyl groups may be substituted with, for example, oxygen or halogen. n is an integer, which may suitably have a value in the range from 1 to 4, and is typically 1.

Suitable diolefins having the formula (II) include 1,4-hexadiene (1,4-HD), 4-methyl-1,4-hexadiene (4M-1,4-HD), 2,4-dimethyl-1,4-hexadiene (2,4DM-1-HD) and 2-methyl-1,4-hexadiene (2M-1,4-HD). Preferred olefins having the formula (II) include 2-methyl-1,4-hexadiene which when reacted with ethylene produce 2-methyl-1,4-pentadiene. Diolefins having the formula (II) may suitably be prepared by codimerisation of simple olefin/diolefin feedstocks or by oxidative dimerisation.

2M-1,4-HD and 4M-1,4-HD may be obtained by any suitable method. A preferred method is to react preferably in the liquid phase in the presence of a catalyst comprising a homogeneous transition metal complex and a reducing agent either (a) butadiene with propene to give 2M-1,4-HD or (b) isoprene with ethylene to give 4M-1,4-HD under appropriate reaction conditions.

A process for the production of hexadienes or alkyl or phenyl derivatives thereof is described for example in GB-A-1,111,508. The process comprises reacting an alpha-olefin with a conjugated diolefinic hydrocarbon in the presence of a catalytic amount of a three component catalyst comprising:

1. an acetylacetonate of the formula:

$$M(C_5H_7O_2)_n$$

or a halide of the formula $MX_n$ where M is the metal cobalt or iron, n is the valence of said metal and where X is a halogen atom:

2. an organophosphorus compound of the formula:

(a) $R_2P-R^1{}_n-PR_2$ or (b) $R_2PO-R^1-POR_2$ where R is an alkyl or aryl group, $R^1$ is an alkylene, alkenylene or arylene group and n is 0 or 1; and 3. at least one organoaluminium compound of the formula:

$$R^{11}{}_m AlZ_{3-m}$$

where $R^{11}$ is a monovalent hydrocarbon group, Z is a hydrogen or halogen atom and m is a number from 1 to 3.

The process of GB-A-1,111,508 may be used for the production of either 2M-1,4-HD or 4M-1,4-HD, useful as feedstocks in the process of the present invention.

Another process for the production of 1,4-hexadiene is described in, for example, U.S. Pat. No. 3,647,902. In this process ethylene and 1,3-butadiene are reacted under pressure in a solvent and in an inert atmosphere in the presence of a catalytic system composed of Co (11) chloride and 1,2-bis(diphenylphosphino)ethane and triethyl aluminium using 1,2-dichloroethane as the sole solvent and using a molar ratio of triethyl aluminium to cobalt (11) chloride of at least 200, the reaction mixture being brought to a temperature of at least about 80° C. before the reaction of the ethylene with the 1,3-butadiene occurs. The process of U.S. Pat. No. 3,647,902 may be applied to the production of either 2M-1,4-HD or 4M-1,4-HD, useful as feedstocks in the process of the present invention.

A preferred catalyst for use in both (a) and (b) above is either a Co (II) salt, for example the chloride or other halide, or an Fe (II) salt, for example the chloride or other halide, in the presence of a ligand comprising either a chelating diphosphine, diarsine or substituted phosphine with a ligating pendant group and a reducing agent which may suitably be an alkyl aluminium or other metal alkyl species. A more preferred catalyst is cobalt chloride, 1,2-diphenylphosphinoethane (DPPE) and triethyl aluminium. In the latter catalyst, the molar ratio of cobalt salt to triethyl aluminium may suitably be 1:greater than 10, preferably 1:greater than 50 and the molar ratio of cobalt chloride to DPPE may suitably be 1:1 to 2, for example as $CoCl_2(DPPE)_2$. The ratio of catalyst to the diolefin may suitably be in the range from 1:1000 to 100,000 and the monoolefin to diolefin ratio may suitably be in the range from 1 to 2:1.

In general, the catalyst may be prepared by mixing the metal salt and the phosphine ligand in a suitable solvent, adding the alkyl aluminium reducing agent and, after the passage of a suitable interval of time adding a diolefin, which may be the same or different to the diolefin reactant, the molar ratio of diolefin to metal salt being greater than 10:1.

The reactions (a) and (b) may be carried out in the presence of a suitable solvent. The solvent may suitably be a halohydrocarbon, preferably chlorobenzene, though non-halogenated solvents, for example toluene, may also be used.

The reaction temperature may suitably be in the range from 15° to 250° C., preferably from 80° to 150° C., more preferably from 90° to 110° C. The choice of reaction temperature influences inter alia the extent of undesirable oligomerisation and isomerisation reactions. For reactions involving ethylene, the pressure may suitably be in the range from 5 to 100 bar, preferably from 30 to 60 bar. For reactions involving propene, the pressure may suitably be in the range from 5 to 40 bar. In either case additional inert gas, for example nitrogen, overpressure may be used.

The reactions (a) and (b) may be operated batchwise or continuously.

As regards the disproportionation reaction, ethylene is commercially available on a large scale and may be used with or without further purification.

The disproportionation catalyst comprises rhenium heptoxide supported on a suitable support as described in, for example, published GB Patents Nos. 1054864, 1064829, 1106015, 1089956, 1103976, 1121806, 1123500, 1159055, 1159053, 1159056, 1170498, 1279254 and 1414488. The support may be any refractory metal oxide, for example alumina, silica, silica-alumina, titania, zirconia, thoria, and the like. A preferred support is alumina and gamma-alumina is most preferred. The alumina may be used in phosphated form, for example as described in the aforesaid GB-A-1414488, or in acid-treated form, or in any other form which facilitates the disproportionation reaction. The loading of rhenium heptoxide on the support may be in the range from 0.1 to 50% by weight, preferably from 1 to 25% by weight.

The supported catalyst may be prepared by any of the methods conventionally employed for the production of supported metal catalysts. Suitable methods include (i) dry mixing of the individual components, (ii) coprecipitation of the catalytic metal and the support, (iii) impregnation of the support with thermally decomposable substances to leave the catalytic metal deposited on the support, (iv) sublimation of sublimable compounds, for example rhenium heptoxide on to the support and (v) reaction of a compound of the catalytic metal with surface hydroxyl groups of a support material to produce a surface bound compound.

A promoter is used in combination with the disproportionation catalyst. The promoter is either a tetralkyl tin compound or a triaalkyl aluminium compound. The alkyl groups of the tetraalkyl tin compound or the trialkyl aluminium compound may suitably be $C_1$ to $C_4$ alkyl groups. Examples of suitable promoters include tetramethyl tin and triethyl aluminium. The preferred promoters are tetraalkyl tin compounds. The promoter may be added to the catalyst in a number of ways. Amongst these may be mentioned (a) direct mixing of the promoter and the catalyst, (b) mixing of the promoter and catalyst in a solvent with subsequent removal of solvent, and (c) direct addition of the promoter to the reaction mixture.

The process may be operated in the gaseous or liquid phase. preference for either one of these phases will generally be determined by the overall economics of the process and the particular catalyst selected.

In the liquid phase, the process may be operated in the presence or absence of a solvent, preferably in the presence of a solvent. Suitably the solvent may be any liquid hydrocarbon which does not have a deleterious effect on the catalyst. Suitable hydrocarbon solvents include alkanes, for example n-heptane, n-octane or isooctane, and aromatic hydrocarbons, for example toluene or xylene. It is preferred to use a solvent with a boiling point intermediate between the diolefin products and other (higher boiling) intermediates. An advantage of this in terms of process operation is to allow product diolefin to be removed by distillation, with recycle of the other intermediates in the reaction solvent.

The diolefin of formula (II) may be reacted with ethylene at a temperature suitably in the range from $-10°$ to $+100°$ C., more preferably from $+10°$ to $+100°$ C., and a pressure in the range from atmospheric to 50 bar. The reaction rate and conversion depend (at least in part) on the ethylene to diolefin feedstock ratio. Higher ratios of ethylene to diolefin feedstock may require higher operating pressures and are expected to favour higher conversions and reaction rates.

The process of the invention may be operated batchwise or continuously, preferably continuously.

The invention will now be further illustrated by reference to the following Examples.

PREPARATION OF METHYL 1,4-HEXADIENES

Example 1—Reaction of Isoprene with Ethylene to give 4M-1,4-HD 1.2 g 1,2- Diphenylphosphinoethane and 0.2 g cobalt (II) chloride were stirred with 19 ml chlorobenzene. After 2 hours had elapsed 12 ml triethyl aluminium in 7 ml toluene was added. After a further 3 hours half of this mixture was added to 150 ml isoprene and then charged to a 500 ml rocking autoclave. The autoclave was pressurised with 38 barg ethylene and heated at 95° C. for 4.5 hours with continuous agitation. After cooling and depressurising 153 g liquid product was recovered. This was analysed by gas chromatography (GC) and shown to contain 71.9% w/w 4M-1,4-HD and 11.7% 5-methyl-1,4-hexadiene. Isoprene conversion was greater than 99% with greater than 95% selectivity to methyl-1,4-hexadienes.

Example 2—Reaction of Butadiene with Propene to give 2M-1,4-HD

The catalyst (half of the mixture prepared in Example 1) was added to 5 ml isoprene 15 minutes after the addition of the triethyl aluminium and toluene components and then charged to a 500 ml rocking autoclave. The autoclave was further charged with 150 ml butadiene followed by 150 ml propene. The reactor was then heated at 90° C. for 4.5 hours with continuous agitation. After cooling and depressurising, 143 g liquid product was recovered. This was analysed by GC and shown to contain 42.5% w/w 2M-1,4-HD. Butadiene conversion was 85% with 42.6% selectivity to 2M-1,4-HD.

2. DISPROPORTIONATION

(A) Preparation of Rhenium Heptoxide on Alumina Catalysts

(a) Preparation of gamma-alumina

Boehmite alumina (CATAPAL SB) was dried at 100° C. in vacuo, pelleted and crushed to give granules of 1 to 2 mm in size. These granules were heat treated to 580° C. in dry flowing air for 24 hours.

(b) Preparation of Phosphated gamma-alumina

A solution of diammonium hydrogen orthophosphate (15 g in 300 ml deionised water) was added to gamma-alumina (100 g prepared as above) and then placed on a steam bath for 6 hours at 80° C. The mixture was stirred and kept moist by occasional addition of deionised water. The alumina was then transferred to a 710 micron sieve, washed thoroughly with deionised water and dried in an oven at 120° C. for 24 hours. The resulting material was then heat treated at 580° C. in flowing dry air for 24 hours.

(c) Preparation of 6% Rhenium Heptoxide on gamma-alumina

A solution of ammonium perrhenate (7.1 g in 100 ml of deionised water) was added to gamma-alumina or the Phosphated gamma-alumina of (b) above (100 g prepared as above) and then placed on a steam bath for 6 hours at 80° C. The mixture was stirred and kept moist by the occasional addition of deionised water. It was then dried at 80° C. for 1 hour and then at 110° C. in vacuo for g hours. It was then sieved to give granules of 1 to 2 mm in size. The catalyst was then activated in dry flowing air for 24 hours at 580° C. The activated catalyst was rapidly cooled to room temperature, purged with dry nitrogen and transferred to a glass storage vessel under nitrogen.

(d) Batch Disproportionation of 2M-1,4-HD or 4M-1.4-HD in o-xylene Solvent

EXAMPLES 1 TO 6

A 0.5 liter Parr autoclave was charged under nitrogen with 6% $Re_2O_7$/gamma-$Al_2O_3$, tetramethyl tin promoter, o-xylene and either 2M-1,4-HD or 4M-1,4-HD and then pressurised with ethylene. The autoclave was then agitated at a set temperature for approximately 16 hours. At the end of this time the liquid product was analysed by gas chromatography. In all cases the major liquid product was the desired 2M-1,4-PD, other products being $C_7$ isomers and $C_{10}$, $C_{11}$ and $C_{12}$ homodismutation products. Examples of conversions and selectivities achieved are given in the Table.

Comparison Test

The procedure of Examples 1 to 6 was repeated except that no tetramethyl tin promoter was added.

The results are given in the Table.

This is not an example according to the present invention because no promoter was employed. It is included only for the purpose of comparison.

EXAMPLE 7

A 0.5 liter Parr autoclave was charged under nitrogen with 6% $Re_2O_7$/gamma-alumina (25 ml), and then pressurised with ethylene to 69 barg. The autoclave was then agitated at 25° C. for 17 hours. At the end of this time the liquid produce was analysed by gas chromatography. 1,4-hexadiene conversion was 98.6% with 21.4% selectivity to pentadiene.

(e) Continuous Disproportionation of 2M-1,4-HD in o-xylene Solvent

A 6% $Re_2O_7$/gamma-alumina catalyst (100 ml) was treated with tetramethyl tin (1.0 ml) and then charged to the reactor of a continuous unit. 6 liters of hydrocarbon feed containing 40.2% 2-M-1,4-HD and 54.6% o-xylene were charged to the feed tank of the continuous unit. The feed tank was then pressurised with ethylene to 600 psig giving a volume increase of about 3 liters. This feed was then passed over the catalyst/promoter at 865 psig, about 15° C. and a liquid hourly space velocity of 2. After 11 hours on stream the product contained 12.1% 2-methyl-1,4-pentadiene and 11.2% 2-methyl-1,4-hexadiene.

TABLE

| Example | Reactants (ml) 2M-1,4-HD | 4M-1,4-HD | o-xylene | Catalyst | Promoter | Ethylene Pressure (barg) | Temp. (°C.) | Run Time (hours) | Conversion of 2M-1,4-HD or 4M-1,4-HD (%) | Selectivity to 2M-1,4-PD (%) |
|---|---|---|---|---|---|---|---|---|---|---|
| 1 | — | 50 | 50 | 25 | 0.25 | 55 | 50 | 16 | 88 | 20 |
| 2* | — | 50 | 50 | 25* | 0.25 | 52 | 50 | 16 | 74 | 30 |
| 3 | 100 | — | 100 | 25 | 0.25 | 49 | 25 | 17 | 89 | 57 |
| 4 | 100 | — | 100 | 25 | 0.25 | 48 | 25 | 17 | 91 | 57 |
| 5 | 100 | — | 100 | 25 | 0.25 | 47 | 50 | 17 | 89 | 58 |
| 6 | 5 | — | 45 | 5 | 0.05 | 42 | 20 | 17 | 88 | 77 |
| Comp Test | 5 | — | 45 | 5 | — | 40 | 20 | 17 | 31 | 24 |

Catalyst:
6% Rhenium Heptoxide on Alumina
*6% Rhenium Heptoxide on Phosphated Alumina.
Promoter: Tetramethyltin.

I claim:

1. A process for the production of a non-conjugated diolefin having the formula:

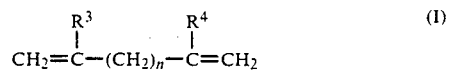

wherein $R^3$ and $R^4$ are either hydrogen, alkyl or substituted alkyl and n is an interger, which process comprises reacting a diolefin having the formula:

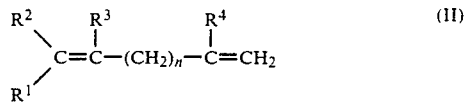

wherein $R^3$ and $R^4$ and n are the same as in formula (I) and $R^1$ and $R^2$ are either hydrogen, alkyl or substituted alkyl, with ethylene in the presence of a disproportionation catalyst which has been prepared by mixing (a) a disproportionation catalyst comprising rhenium heptoxide supported on a support comprising alumina and (b) a promoter selected from either a tetralkyl tin compound or a trialkyl aluminum compound.

2. A process according to claim 1 wherein the diolefin having the formula (II) is either 1,4-hexadiene, 4-methyl-1,4-hexadiene, 2,4-dimethyl-1,4-hexadiene or 2-methyl-1,4-hexadiene.

3. A process according to claim 1, wherein the diolefin having the formula (II) is 2-methyl-1,4-hexadiene and the non-conjugated diolefin product is 2-methyl-1,4-pentadiene.

4. A process according to claim 1 wherein the diolefin having the formula (II) is obtained by reacting in the liquid phase in the presence of a catalyst comprising the homogenous transition metal complex and a reducing agent either (a) butadiene with propene to give 2M-1,4-HD or (b) isoprene with ethylene to give 4M-1,4-HD.

5. A process according to claim 1, wherein the disproportionation catalyst is rhenium heptoxide supported on a gamma-alumina.

6. A process according to claim 1, wherein the promoter is a tetralkyl tin compound.

7. A process according to claim 1, wherein the tetralkyl tin compound is tetramethyl tin.

8. A process according to claim 1, wherein the reaction is effected in the presence of a hydrocarbon solvent.

9. A process according to claim 7, wherein the hydrocarbon solvent is ortho-xylene.

10. A process according to claim 1, wherein the reaction is effected at a temperature in the range from −10° to +100° C. and a pressure in the range from atmospheric to 50 bar.

11. A process for the production of a non-conjugated diolefin having the formula:

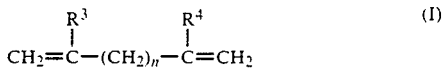

wherein $R^3$ and $R^4$ are either hydrogen, alkyl or substituted alkyl and n is an integer, which process comprises reacting a diolefin having the formula:

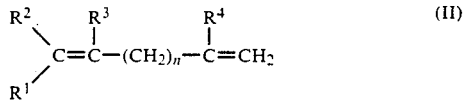

wherein $R^3$ and $R^4$ and n are the same as in formula (I) and $R^1$ and $R^2$ are either hydrogen, alkyl or substituted alkyl, with ethylene in the presence of a catalyst which has been prepared by depositing (a) a promoter comprising either a tetralkyl tin compound or a trialkyl aluminum compound onto (b) a disproportionation catalyst comprising rhenium heptoxide supported on a support comprising alumina.

12. A process for the production of a non-conjugated diolefin having the formula:

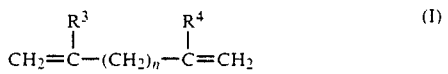

wherein R³ and R⁴ are either hydrogen, alkyl or substituted alkyl and n is an integer, which process comprises reacting a diolefin having the formula:

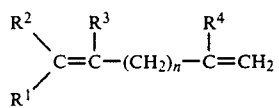 (II)

wherein R³ and R⁴ and n are the same as in formula (I) and R¹ and R² are either hydrogen, alkyl or substituted alkyl, with ethylene in the presence of a reaction mixture of (a) a disproportionation catalyst comprising rhenium heptoxide supported on a support comprising alumina catalyst and (b) a promoter comprising either a tetralkyl tin compound or a trialkyl aluminum compound, wherein said promoter has been added to the reaction mixture.

* * * * *